United States Patent [19]
Mueller et al.

[11] Patent Number: 5,811,386
[45] Date of Patent: Sep. 22, 1998

[54] CLEAR SURFACE-ACTIVE MIXTURES CONTAINING ANIONIC SURFACTANT, APG, AND TEMPORARILY CATIONIC COPOLYMER

[75] Inventors: Reinhard Mueller, Erkelenz; Kurt Seidel, Duesseldorf; Detlef Hollenberg, Erkrath; Manuela Ehlert, Leverkusen, all of Germany

[73] Assignee: Henkel Kommanditgesellschaft auf Aktien, Duesseldorf, Germany

[21] Appl. No.: 903,683

[22] Filed: Jul. 31, 1997

Related U.S. Application Data

[63] Continuation of Ser. No. 495,537, filed as PCT/EP94/00133, Jan. 20, 1994, published as WO94/16679, Aug. 4, 1994, abandoned.

[30] Foreign Application Priority Data

Jan. 28, 1993 [DE] Germany ............... 43 02 315.0

[51] Int. Cl.⁶ .................. C11D 1/83; C11D 3/22; C11D 3/37; A61K 7/075
[52] U.S. Cl. .............. 510/535; 510/123; 510/125; 510/126; 510/127; 510/159; 510/427; 510/470; 510/475; 510/476; 510/499; 510/537
[58] Field of Search .................. 510/535, 537, 510/123–128, 135, 159, 499, 504, 470, 427–429, 475, 476; 424/70.19, 70.22, 70.24, 70.27, 70.31

[56] References Cited

U.S. PATENT DOCUMENTS

| | | | |
|---|---|---|---|
| 3,547,828 | 12/1970 | Mansfield et al. | 252/351 |
| 3,707,535 | 12/1972 | Lew | 260/210 R |
| 3,839,318 | 10/1974 | Mansfield | 260/210 R |
| 3,954,960 | 5/1976 | Valan | 424/47 |
| 4,165,367 | 8/1979 | Chakrabarti | 424/47 |
| 4,223,009 | 9/1980 | Chakrabarti | 424/47 |
| 4,477,375 | 10/1984 | Grollier | 252/542 |
| 4,540,507 | 9/1985 | Grollier | 252/174.23 |
| 4,773,939 | 9/1988 | Meffert et al. | 134/10 |
| 4,842,849 | 6/1989 | Grollier et al. | 424/70.13 |
| 5,057,311 | 10/1991 | Kamegai et al. | 424/70.13 |
| 5,208,014 | 5/1993 | Dubief et al. | 424/70.51 |
| 5,294,726 | 3/1994 | Behler et al. | 554/98 |
| 5,409,628 | 4/1995 | Heinz et al. | 252/174.17 |
| 5,422,031 | 6/1995 | Nomura et al. | 252/174.17 |

FOREIGN PATENT DOCUMENTS

| | | |
|---|---|---|
| 0077167 | 4/1983 | European Pat. Off. . |
| 0299370 | 1/1989 | European Pat. Off. . |
| 0337354 | 10/1989 | European Pat. Off. . |
| 1943689 | 3/1970 | Germany . |
| 2036472 | 2/1971 | Germany . |
| 2150557 | 6/1972 | Germany . |
| 3001064 | 7/1981 | Germany . |
| 3336760 | 4/1984 | Germany . |
| 3926344 | 2/1991 | Germany . |
| 9110351 | 12/1992 | Germany . |
| 4207046 | 9/1993 | Germany . |
| 2117784 | 10/1983 | United Kingdom . |

OTHER PUBLICATIONS

Soap, Cosmet. Chem. Spec. vol. 56, No. 2, 1980, NJ, US; E.J. Murphy 'Cationic Polymer Conditioner Evaluation' see pp. 34; 39–40; 82.
Soap/Cosmetics/Chemical Specialities, Jan. 1988, pp. 34–36; 74.
Seifen–Öle–Fette–Wachse 1990 (116) 60.
"Kosmetik—Entwicklung, Herstellung und Anwendung kosmetischer Mittel", pp. 86–87, Stuttgart 1988.
"Kosemetika, Riechstoffe und Lebensmittelzusatztoffe" Stuttgart 1978.
Farbstoff–Kommission der Deutschen Forschungsgemeinschaft für Kosmetika ("Färbemittel für Kosmetika" Mitteilung 3, Wiesbaden 1968).
J. Soc. Cosmet. Chem., 24, 773–782 (Dec. 9, 1973).

*Primary Examiner*—Ardith Hertzog
*Attorney, Agent, or Firm*—Wayne C. Jaeschke; John E. Drach; Henry E. Millson, Jr.

[57] ABSTRACT

A surface active mixture comprising: (A) from about 1 to about 50% by weight of an anionic surfactant having one or two lipophilic groups and having from 1 to 22 carbon atoms and a polar group selected from the group consisting of carboxylate, sulfate and sulfonate groups; (B) from about 0.5 to about 15% by weight of an alkyl glycoside of the formula $R(G)_x$, wherein R is a linear saturated alkyl radical having from 8 to 22 carbon atoms and $(G)_x$ is a glycoside or oligoglycoside unit with a degree of oligomerization x of 1 to 10; (C) from about 0.1 to about 7% by weight of a nitrogen-containing copolymer having a molecular weight of from about 15,000 to about 1,500,000 wherein said copolymer is comprised of: (i) from about 99.5 to about 45 mole-% of units derived from vinyl pyrrolidone, (ii) from at 0.5 to about 50 mole-% of units derived from a monomer corresponding to formula (I):

$$CH_2=CHR^1-COOR^2-NR^3R^4 \qquad (I)$$

$R^1$ is hydrogen or methyl, $R^2$ is a $C_{1-20}$ alkylene group and each of $R^3$ and $R^4$ is independently a $C_{1-4}$ alkyl group and, (iii) from 0 to about 50 mole-% of units derived from at least one ethylenically unsaturated copolymerizable monomer different from (i) and (ii), and; (D) from about 28 to about 98.4% by weight of water with the proviso that: (a) the pH value of the mixture Is in the range from 3 to 7 so that the copolymer (C) is present in temporarily cationic form, (b) the sum of components (B) and (C) is no greater than the content of component (A) and, (c) the mixture is free from nitrogen-containing copolymers wherein the nitrogen atoms are present at least partly in permanent cationic form.

15 Claims, No Drawings

CLEAR SURFACE-ACTIVE MIXTURES CONTAINING ANIONIC SURFACTANT, APG, AND TEMPORARILY CATIONIC COPOLYMER

This application is a continuation of application Ser. No. 08/495,537, filed as PCT/EP94/00133, Jan. 20, 1994, published as WO94/16679, Aug. 4, 1994, now abandoned.

BACKGROUND OF THE INVENTION

Field of the Invention

This invention relates to surface-active mixtures, more particularly formulations for the washing or rinsing of hair, of which the composition makes them particularly compatible with the skin.

STATEMENT OF RELATED ART

Prior Art

To enable them to develop a cleaning effect, water-based cleaning formulations typically contain surface-active compounds which generally have an adverse effect on the skin. This applies in particular to the important class of anionic surfactants.

This adverse effect on the skin should be avoided in the field of body-care formulations. Compatibility with the skin is particularly important for cleaning products which are designed for frequent use, which are intended for intimate parts of the body or which come into contact with the mucosa. Accordingly, there is a constant need for mild water-based cleaning formulations with good foaming power.

Formulations for washing or rinsing hair, for example shampoos and rinsable hair aftertreatment preparations, are of particular interest in the field of water-based cleaning formulations. In particular, there is a constant need for formulations which have an improved effect on hair in terms of body and stylability.

The hair is often in a cosmetically unsatisfactory state after washing. It feels dull, is difficult to comb when wet and tends to develop static charges when dry which makes the hair difficult to comb and affects the way the combed hair lies.

The use of zwitterionic polymers containing anionic groups, generally carboxyl groups and quaternary ammonium groups in the molecule in hair treatment formulations is already known. For example, DE-OS 21 50 557 describes the use of polymers of zwitterionic monomers in hair setting formulations. Unfortunately, zwitterionic polymers have the disadvantage, especially in formulations containing anionic surfactants, that the hair-conditioning and hair-setting properties are generally lost after prolonged storage.

DE 33 36 760 C2 (L'Oreal) describes mild cleaning formulations containing glucoside alkyl ethers with $C_{8-10}$ alkyl radicals and nonionic polymers, such as polyvinyl pyrrolidone or copolymers thereof with nonionic co-monomers.

It is also known that conditioning preparations, generally based on cationic surfactants, can be applied to the hair after washing or shampooing or that conditioners can be added to shampoos in order to obtain a certain conditioning effect when the hair is washed. Corresponding substances are, for example, cationic polymers, such as cationic cellulose derivatives.

Thus, EP 337 354 (Kao) describes formulations containing a combination of alkyl glycosides and at least one cationic polymer. According to the definition of the problem in EP 337 354, formulations which are kind to the skin and which develop a certain foaming power are supposed to be obtained with this combination.

The cationic polymers to be used according to the teaching of EP 337 354 are essentially substances which are permanently cationic, i.e. of which the molecular structure is such that, on the one hand, it contains a polymeric moiety with permanent cationic centers and, on the other hand, corresponding counterions of anionic character. "Permanent" in this context means that the positive charges at the hetero atoms, such as nitrogen, are immutably fixed. A typical example of corresponding substances are the known quaternary ammonium salts in which the nitrogen is attached to four organic radicals. Accordingly, the positive charge of the nitrogen is permanent and remains intact as long as the compound is not chemically modified, i.e. as long as the degree of substitution of the nitrogen is not altered by chemical reaction.

DESCRIPTION OF THE INVENTION

However, the requirements which the surface-active mixtures according to the invention are expected to satisfy are not confined to the skin-friendly properties or to a certain foaming power. Instead, there are a number of other requirements to be satisfied.

Although a satisfactory improvement in wet combability and a reduction in static charging are obtained with the formulations known from the prior art, cf. in particular EP 337 354, these effects are almost always accompanied by excessive smoothing of the dry hair. This means that the hair lacks body and is not receptive to styling. The smoothness of the hair is more pronounced, the lower the combing resistance of the dry hair.

In addition, it has been found that water-containing compositions based on permanent cationic polymers are generally cloudy, a fact which is unwanted from the applicational point of view because clear products are preferred.

Accordingly, the problem addressed by the present invention was to provide surface-active mixtures and, more particularly, formulations for the washing and rinsing of hair which, for good foaming power and a minimal effect on the skin, would improve the stylability and style retention of hair without making the hair tacky. In addition, the mixtures would not have any tendency towards clouding, but instead would be present in clear form.

It has now surprisingly been found that the body, stylability and style retention of hair can be distinctly improved by comparison with the prior art providing the surface-active mixture contains 1 to 50% by weight of an anionic surfactant, 0.5 to 15% by weight of an alkyl glycoside and 0.1 to 7% by weight of a special temporary cationic copolymer.

Accordingly, the present invention relates to surface-active mixtures containing (A) 1 to 50% by weight of one or more anionic surfactants containing one or two lipophilic groups containing 1 to 22 carbon atoms and a polar group selected from carboxylate, sulfate or sulfonate groups and optionally a polyoxyalkylene group with an average degree of alkoxylation of 1 to 15, (B) 0.5 to 15% by weight of one or more alkyl glycosides corresponding to the general formula $R(G)_x$, where R is a linear saturated alkyl radical containing 8 to 22 carbon atoms and $(G)_x$ is a glycoside or oligoglycoside unit with a degree of oligomerization x of 1 to 10, (C) 0.1 to 7% by weight of a nitrogen-containing copolymer with a molecular weight of around 15,000 to 1,500,000 which contains (i) 99.5 to 45 mole-% of units derived from vinyl pyrrolidone, (ii) 0.5 to 50 mole-% of units derived from a monomer corresponding to formula (I):

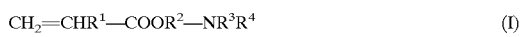

$$CH_2=CHR^1-COOR^2-NR^3R^4 \qquad (I)$$

in which —$R^1$ is hydrogen or methyl,
—$R^2$ is a $C_{1-20}$ alkylene group and
—$R^3$ and $R^4$ independently of one another represent a $C_{1-4}$ alkyl group,
and (iii) 0 to 50 mole-% of units derived from at least one ethylenically unsaturated copolymerizable monomer different from (i) and (ii), and (D) 28 to 98.4% by weight of water, with the proviso that a) the pH value of the mixture is in the range from 3 to 7 so that the polymer (C) is present in temporarily cationic form, b) the sum of components (B) and (C) is no greater than the content of component (A) and c) the mixture is free from nitrogen-containing polymers and/or permanently cationic copolymers.

A polyoxyalkylene group is understood to be a group made up of oxyethylene units —[$CH_2$—$CH_2$—O]— or of oxypropylene units —[$CH(CH_3)$—$CH_2$—O]—. As generally known among experts, the average degree of alkoxylation is understood to be the average number of oxyalkylene units per molecule of the anionic surfactant.

According to the invention, the anionic surfactants (A) are preferably selected from the group of alkyl and dialkyl ether sulfates, ether carboxylic acids, sulfosuccinic acid semiesters, fatty alcohol ether citrates, fatty alcohol ether tartrates, acyl sarcosides, acyl taurides, acyl isethionates and the sulfonates of unsaturated fatty acids.

The counterions of the carboxylate, sulfate or sulfonate groups are preferably selected from alkali and alkaline earth metals, aluminium, ammonium and alkyl or alkylol ammonium groups containing 1 to 4 carbon atoms in each alkyl or alkylol group. The group of alkali metals is most particularly suitable.

The chemical structures and the basic surfactant properties of most of these anionic surfactants are now textbook knowledge and, accordingly, do not require any further explanation. Other suitable anionic surfactants are mentioned in the following. Dialkyl ether sulfates are understood to be compounds of the type described in EP 299 370. Particulars of the production process and properties of these compounds can be found in that document. Fatty alcohol ether tartrates are under to be monoester salts of tartaric acid while fatty alcohol ether citrates are understood to be monoester and/or diester salts of citric acid with adducts of ethylene oxide and/or propylene oxide with fatty alcohols. Sulfonates of unsaturated fatty acids are understood to be sulfonation products of fatty acids containing 12 to 22 carbon atoms and 1 to 6 double bonds. Products such as these are known from the literature and may be obtained, for example, by reaction of these fatty acids with gaseous sulfur trioxide. Particulars of the production process using oleic acid, for example, can be found in DE-A-39 26 344.

In the case of anionic surfactants containing a polyoxyalkylene group, it may be said quite generally with regard to the degree of alkoxylation that alkoxylation reactions such as, for example, the addition of x moles of ethylene oxide onto 1 mole of fatty alcohol by known methods of ethoxylation do not give an individual adduct, but rather a mixture of residual quantities of free fatty alcohol and a number of homologous (oligomeric) adducts of 1, 2, 3, . . . x, x+1, x+2 . . . etc. molecules of ethylene oxide per molecule of fatty alcohol. The average degree of ethoxylation (x) is defined by the starting quantities of fatty alcohol and ethylene oxide. The distribution curve of the homolog mixture generally has a maximum between x−3 and x+3. Further information on this subject can be found, for example, in the journal Soap/Cosmetics/Chemical Specialities, January 1988, page 34. However, in addition to the usual alkoxylation catalysts known from the prior art, such as sodium methanolate, it is also possible to use catalysts which lead to so-called narrow-range products, cf. for example Seifen-öle-Fette-Wachse 1990 (116) 60.

In one preferred embodiment of the invention, the percentage content of anionic surfactants is 4 to 30% by weight.

Alkyl glycosides (B) corresponding to the general formula R—$(G)_x$ are well-known surface-active substances which can be obtained by acetalization from sugars and aliphatic primary alcohols containing 8 to 22 carbon atoms. Preferred sugar components (glycose) are glucose and also fructose, mannose, galactose, talose, gulose, allose, altrose, idose, arabinose, xylose, lyxose, libose and mixtures thereof.

Acetalization products of glucose with fatty alcohols R—OH, obtainable for example from natural fats and oils by known methods, more particularly with linear, primary, saturated and unsaturated $C_{8-22}$ fatty alcohols are preferred by virtue of their ready availability and their favorable performance properties.

Alkyl glycosides, their production and their use as surface-active substances are known, for example, from U.S. Pat. Nos. 3,839,318, 3,707,535, 3,547,828, DE-A-19 43 689, DE-A-20 36 472, DE-A-30 01 064 and EP-A-77 167. So far as the glycoside unit —$(G)_x$ is concerned, both monoglycosides (x=1), in which a sugar unit is attached to the fatty alcohol by a glycoside bond, and oligomeric glycosides with a degree of oligomerization x of 2 to 10 are suitable. Mixtures of monoglycosides and oligoglycosides are generally present. Alkyl glycosides (B), in which R is an alkyl group containing 8 to 22 carbon atoms and $(G)_x$ is a glycoside or oligoglycoside unit with a degree of oligomerization x of 1 to 10, are particularly suitable. In a particularly preferred embodiment, R is an alkyl group containing 10 to 16 carbon atoms while $(G)_x$ is the residue of a mixture of glucoside and oligoglucosides with an average degree of oligomerization of 1 to 1.5.

In one preferred embodiment of the invention, the percentage content of alkyl glycoside is 1 to 8% by weight.

As already mentioned, only those nitrogen-containing copolymers (C) which are present in temporarily cationic form at a pH value of the formulation of 3 to 7 are suitable for the purposes of the invention. It is specifically pointed out once again at this juncture that nitrogen-containing copolymers, of which the N atoms are present at least partly in permanently cationic form, are not among the copolymers (C) which may be used in accordance with the invention.

In accordance with the above definition of a "permanently" cationic polymer, it is pointed out in this connection that a "temporarily" cationic form of a nitrogen-containing copolymer is present when the magnitude of the positive charge of the nitrogen atoms can readily be modified, for example by adjusting the pH value of the aqueous mixture. Structurally, this is made possible by the fact that the nitrogen atoms of the corresponding polymers are attached to only three organic radicals. By adjusting an acidic pH value, the nitrogen is positively charged. However, this charge can be removed again by altering the pH to an alkaline value without affecting the structure of the polymer.

Copolymers (C) of vinyl pyrrolidone and dimethylaminoethyl methacrylate, which are characterized by the structure (I-a):

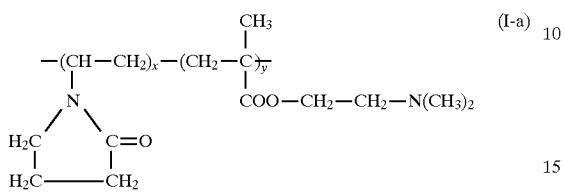

in which x and y are selected within the limits defined in the foregoing so that the compounds have a molecular weight of 15,000 to 1,500,000, have proved to be particularly suitable. Some of these products are commercially available, for example "Copolymer 937".

In one preferred embodiment of the invention, the percentage content of the temporary cationic polymer (C) is 0.5 to 5% by weight.

In addition to the anionic surfactants (A), the formulations according to the invention may also contain 0.5 to 20% by weight and, more particularly, 1 to 10% by weight of ampholytic and/or zwitterionic surfactants.

Ampholytic surfactants are understood to be surface-active compounds which, in addition to a $C_{8-18}$ alkyl or acyl group in the molecule, contain at least one free amino group and at least one —COOH— or —$SO_3H$— group and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkyl-amidopropyl glycines, N-alkyl taurines, N-alkyl sarcosines, 2-alkylaminopropionic acids and alkylaminoacetic acids containing around 8 to 18 carbon atoms in the alkyl group.

Zwitterionic surfactants are surface-active compounds which contain at least one quaternary ammonium group and at least one —$COOH^{(-)}$ or —$SO_3^{(-)}$ group in the molecule. Particularly suitable zwitterionic surfactants are the so-called betaines, such as N-alkyl-N,N-dimethylammonium glycinates, for example cocoalkyl dimethylammonium glycinate, N-acylaminopropyl-N,N-dimethylammonium glycinate, for example cocoacylaminopropyl dimethylammonium glycinate, and 2-alkyl-3-carboxymethyl-3-hydroxyethyl imidazolines containing 8 to 18 carbon atoms in the alkyl or acyl group and cocoacyl aminoethyl hydroxyethyl carboxymethyl glycinate.

The skin-friendly properties of the mixtures according to the invention are particularly noticeable when they are formulated in such a way that they have a pH value in the vicinity of the neutral point of the skin. Mixtures having pH values of 5.0 to 6.5 are preferred.

The mixtures according to the invention may also contain inorganic electrolyte salts (E). Suitable inorganic electrolyte salts are any water-soluble alkali metal, ammonium and alkaline earth metal salts, for example the fluorides, chlorides, bromides, sulfates, phosphates and nitrates and hydrogen carbonates providing they have a solubility in water at 20° C. of at least 1% by weight. The chlorides or sulfates of an alkali metal, ammonium or magnesium are preferably used, sodium chloride and magnesium chloride being particularly preferred. The electrolyte salt is preferably used in a quantity of 0.1 to 10% by weight.

The mixtures according to the invention may be used in a number of cleaning and/or personal-care products, including for example cosmetic formulations, such as hair shampoos, foam baths, shower baths, liquid soaps, rinsable hair aftertreatment formulations, such as hair rinses, hair tonics and the like. They are particularly suitable for mild hair shampoos designed to provide the hair with improved body and stylability. However, the mixtures according to the invention may also be used in manual dishwashing detergents.

In addition to surfactants or surfactant combinations, these products normally contain such constituents as emulsifiers, oil components, solubilizers, thickeners, superfatting agents, biogenic agents, film formers, fragrances, dyes, pearlescers, foam stabilizers, preservatives and pH regulators. Accordingly, the mixtures according to the invention may contain additional components and auxiliaries known from the prior art. The most important are:

Nonionic surfactants/emulsifiers, for example ethylene oxide adducts with alcohols, carboxylic acids, partial glycerides and sorbitan esters and, for example, fatty acid esters and sorbitan fatty acid esters (cf. for example W. Umbach [ed.], "Kosmetik - Entwicklung, Herstellung und Anwendung kosmetischer Mittel", pages 86–87, Stuttgart 1988).

Oil components; for example such substances as paraffin oil, vegetable oils, fatty acid esters, squalane and 2-octyl dodecanol; as fats and waxes, for example spermaceti, beeswax, montan wax, paraffin and cetostearyl alcohol.

Solubilizers, for example lower monohydric or polyhydric alcohols, such as ethanol, isopropanol, ethylene glycol, propylene glycol, glycerol, 1,3-butylene glycol and diethylene glycol.

Thickeners, for example polysaccharides, more particularly xanthan gum, guar gum, agar agar, alginates and tyloses, and carboxymethyl cellulose and hydroxyethyl cellulose, relatively high molecular weight polyethylene glycol monoesters and diesters of fatty acids, polyacrylates, polyvinyl alcohol and polyvinyl pyrrolidone.

Superfatting agents, for example polyethoxylated lanolin derivatives, lecithin derivatives and fatty acid alkanolamides, fatty acid alkanolamides also acting as foam stabilizers.

Biogenic agents, such as plant extracts, protein degradation products and vitamin complexes.

Humectants, for example glycerol, polyglycerols, sorbitol, propane-1,2-diol, butane-1,2,3-triol, polyethylene glycols, glucose, mannitol, xylitol, pyrrolidone carboxylic acid salts (PCA), amino acids, lactic acid.

Antimicrobial agents as preservatives, for example benzoic acid, salicylic acid, sorbic acid and esters and salts thereof and also the substances listed in the Appendix to the "Kosmetikverordnung".

Pearlescers, such as glycol distearic acid esters, ethylene glycol distearate or fatty acid monoglycol esters.

Fragrances, for example natural fragrances which are obtained from plants by distillation, extraction or pressing and also synthetic fragrances (cf. for example H. Aebi, E. Baumgartner, H. P. Fiedler, G. Ohloff, "Kosmetika, Riechstoffe und Lebensmittelzusatzstoffe" Stuttgart 1978).

Anitoxidants, for example tocopherols, lecithin, guaiacol, butyl cresol, 4-methyl-2,6-ditert.butylphenol (BHT), 4-methoxy-2(3)tert.butylphenol (BHA).

Dyes of the type listed, for example, by the Farbstoff-Kommission der Deutschen Forschungsgemeinschaft für Kosmetika ("Färbemittel für Kosmetika" Mitteilung 3, Wiesbaden 1968). The dyes are normally used in concentrations of 0.001 to 0.01% by weight, based on the mixture as a whole.

pH regulators: other components of the mixtures according to the invention are, optionally, substances for adjusting the pH value of the mixtures.

The total quantity of auxiliaries is from 0 to 20% by weight and preferably 0 to 10% by weight.

To prepare the mixtures according to the invention, the alkyl glycoside (B) is added at 60° to 80° C. to an aqueous phase containing the anionic surfactants (A) and the synthetic nonionic polymer (C). These mixtures are stirred and then cooled to normal temperature (20° to 40° C.). By virtue of the solubility in water of the alkyl glycosides, especially those containing $C_{12-16}$ alkyl radicals, the mixtures according to the invention may advantageously be produced by the so-called cold route. To this end, the components are simply stirred together at normal temperature.

The following Examples are intended to illustrate the invention without limiting it in any way.

EXAMPLES

1. General

1.1 Abbreviations

In the column headings of Tables 1 and 2, the Example according to the invention is identified as E1 and the Comparison Example as C1.

1.2. Substances used

1.2.1. Surfactants

Dehyton K: Aqueous solution of a fatty acid amide derivative of betaine structure corresponding to the formula R—CONH—$(CH_2)_3$—$N^+(CH_3)_2$—$CH_2$—$COO^-$; CTFA name: Cocamidopropyl Betaine; active substance content: 30% by weight; NaCl content: 5% by weight (a product of Henkel KGaA, Düssel-dorf)

AKYP: Aqueous solution of an ether carboxylic acid salt corresponding to the formula $C_{12/14}$—(O—$CH_2$—$CH_2$—$OCH_2$—COONa, active substance content: 22% by weight ("Akypo® Soft 100 NV", a product of Chemy-Y)

APG 600: $C_{12/14}$ fatty alcohol glucoside with a degree of oligomerization of 1.45 (a product of Henkel KGaA, Düsseldorf)

Texapon K14S: Aqueous solution of sodium lauryl myristyl ether sulfate; active substance content: 28% by weight ("Texapon® K14S", a product of Henkel KGaA, Düsseldorf)

1.2.2. Polymers

COPOLY-1: Copolymer of vinyl pyrrolidone and dimethylaminoethyl methacrylate; molecular weight approx. 1,000,000 ("Copolymer 937", a product of GAF)

COPOLY-2: Copolymer of hydroxyethyl cellulose and diallyl dimethylammonium chloride, CTFA name Polyquaternium-4; active substance content 95% ("Celquat L 200", a product of Delft National)

1.2.3. Other Substances

Nutrilan I: Protein hydrolyzates; CTFA name: Hydrolyzed-Animal-Collagen ("Nutrilan® I", a product of Grñau, Illertissen)

2. Determination of Wet Combability (Test Method)

The combability tests were based on the method according to J. Soc. Cosm. Chem. 1973 [24] 782.

Combability was tested on brown hair (Alkinco #6634, tress length 12 cm, tress weight 1 g). The hair used was slightly predamaged (cold-waved or bleached) as might be expected in the average user. After the zero measurement, the tresses were soaked with 100 ml of the formulation to be tested. After a contact time of 5 minutes, the tresses were rinsed for 1 minute in running water (1 l/min., 38° C.). To determine wet combability, the strands were then remeasured.

3. Test Results

For compositions C1 and E1 described in Table 1 below, wet combability and the appearance of the composition were evaluated. The figures in Table 1 are based on % by weight of active substance.

The tests were carried out by a panel of 6 people with practical experience in the evaluation of hair tresses. The results of the wet combability tests were evaluated on a scale of 1 (very good) to 5 (very poor).

It was found (cf. Table 2) that composition E1 according to the invention in relation to Comparison Example C1 a) is superior in regard to wet combability and b) is clear (as opposed to cloudy) in appearance.

TABLE 1

Compositions C1 and E1

| Substance | C1 | E1 |
|---|---|---|
| Texapon K14S | 42.0 | 42.0 |
| Dehyton K | 10.0 | 10.0 |
| Nutrilan I | 0.5 | 0.5 |
| APG 600 | 2.0 | 2.0 |
| AKYP | 5.0 | 5.0 |
| Copoly-1 | — | 2.0 |
| Copoly-2 | 2.0 | — |
| Na Salicylate | 0.57 | 0.57 |
| NaCl | 1.0 | 1.0 |
| Water | ad 100 | ad 100 |

TABLE 2

Test results C1 and E1

| | C1 | E1 |
|---|---|---|
| Wet combability | 4 | 3 |
| Appearance | Cloudy | Clear |

What is claimed is:

1. A surface active mixture comprising:

(A) from about 1 to about 50% by weight of an anionic surfactant having one or two lipophilic groups and having from 1 to 22 carbon atoms and a polar group selected from the group consisting of carboxylate, sulfate and sulfonate groups;

(B) from about 0.5 to about 15% by weight of an alkyl glycoside of the formula $R(G)_x$, wherein R is a linear saturated alkyl radical having from 8 to 22 carbon atoms and $(G)_x$ is a glycoside or oligoglycoside unit with a degree of oligomerization x of 1 to 10;

(C) from about 0.1 to about 7% by weight of a nitrogen-containing copolymer having a molecular weight of from about 15,000 to about 1,500,000 wherein said copolymer is comprised of:
(i) from about 99.5 to about 45 mole-% of units derived from vinyl pyrrolidone,
(ii) from about 0.5 to about 50 mole-% of units derived from a monomer corresponding to formula (I):

$$CH_2\text{—}CHR^1\text{—}COOR^2\text{—}NR3R^4 \qquad (I)$$

$R^1$ is hydrogen or methyl, $R^2$ is a $C_{1-20}$ alkylene group and each of $R^3$ and $R^4$ is independently a $C_{1-4}$ alkyl group and,
(iii) from 0 to about 50 mole-% of units derived from at least one ethylenically unsaturated copoloymerizable monomer different from (i) and (ii), and,
(D) from about 28 to about 98.4% by weight of water with the proviso that:
(a) the pH value of the mixture is in the range from 3 to 7 so that the copolymer (C) is present in temporarily cationic form,
(b) the sum of components (B) and (C) is no greater than the content of component (A),
(c) the mixture is free from nitrogen-containing copolymers wherein the nitrogen atoms are present at least partly in permanent cationic form, and (d) the mixture is present in clear form at room temperature.

2. The surface active mixture of claim 1 wherein component (A) is present in from about 4 to about 30% by weight, and component (B) is present in from about 1 to about 8% by weight.

3. The surface active mixture of claim 2 wherein component (C) is present in from about 0.5 to about 5% by weight.

4. The surface active mixture of claim 1 wherein the percentage content of said anionic surfactant (A) is from about 4 to about 30% by weight.

5. The surface active mixture of claim 1 wherein the percentage content of said alkyl glycoside (B) is from about 1 to about 8% by weight.

6. The surface active mixture of claim 1 wherein the percentage content of said copolymer (C) is from about 0.5 to about 5% by weight.

7. The surface active mixture of claim 1 wherein component (A) is selected from the group consisting of alkyl other sulfates, dialkyl ether sulfates, ether carboxylic acids, sulfosuccinic acid semiesters, fatty alcohol ether citrates, fatty alcohol ether tartrates, acyl sarcosides, acyl taurides, acyl isethionates and the sulfonates of unsaturated fatty acids.

8. The surface active mixture of claim 7 wherein In component (B), R is an alkyl radical containing from 10 to 16 carbon atoms, and $(G)_x$ is the residue of a mixture of glucoside and oligoglucosides with an average degree of oligomerization of from 1 to about 1.5.

9. The surface active mixture of claim 1 wherein said copolymer (C) is a copolymer of vinyl pyrrolidone and dimethylaminoethyl methacrylate.

10. The surface active mixture of claim 1 wherein said polar group in component (A) is further comprised of a polyoxyalkylene group with an average degree of alkoxylation of 1 to 15.

11. The surface active mixture of claim 1 wherein in component (A), the carboxylate, sulfate or sulfonate group has a counterion which is selected from the group consisting of an alkali metal, an alkaline earth metal, aluminum, ammonium, $C_{1-4}$ alkyl ammonium, and $C_{1-4}$ alkylol ammonium ion.

12. The surface active mixture of claim 1 further comprising from about 0.1 to about 10% by weight of an inorganic electrolyte salt (E).

13. The surface active mixture of claim 1 wherein the pH of the mixture is in the range of from about 5.0 to about 6.5.

14. In a cleaning or personal care product, the improvement wherein a surface-active effective quantity of the surface active mixture of claim 1 is present therein.

15. The product of claim 14 wherein the product is a hair treatment or conditioning composition.

* * * * *